United States Patent
Bruder et al.

(10) Patent No.: US 7,738,686 B2
(45) Date of Patent: Jun. 15, 2010

(54) METHOD FOR OPTIMIZING THE DISPLAY OF FLAT SLICES OF A CYCLICALLY AND COMPLEXLY MOVING EXAMINATION OBJECT FROM DETECTOR MEASURED DATA OF A TOMOGRAPHY UNIT

(75) Inventors: Herbert Bruder, Hoechstadt (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1192 days.

(21) Appl. No.: 11/147,186

(22) Filed: Jun. 8, 2005

(65) Prior Publication Data

US 2005/0276372 A1    Dec. 15, 2005

(30) Foreign Application Priority Data

Jun. 9, 2004    (DE) .................. 10 2004 028 121

(51) Int. Cl.
    *G06K 9/00*    (2006.01)
(52) U.S. Cl. .................. 382/131; 382/128; 382/132
(58) Field of Classification Search ............ 382/128, 382/131, 132
    See application file for complete search history.

(56) References Cited

U.S. PATENT DOCUMENTS

| | | | |
|---|---|---|---|
| 4,937,526 A * | 6/1990 | Ehman et al. ............... 324/309 |
| 6,370,217 B1 * | 4/2002 | Hu et al. .................... 378/8 |
| 6,373,920 B1 * | 4/2002 | Hsieh ................ 378/98.11 |
| 6,381,487 B1 | 4/2002 | Flohr et al. |
| 6,526,117 B1 * | 2/2003 | Okerlund et al. ........... 378/8 |
| 6,539,074 B1 * | 3/2003 | Yavuz et al. ............... 378/4 |
| 6,718,004 B2 | 4/2004 | Cesmeli |
| 6,819,736 B1 | 11/2004 | Bruder et al. |
| 7,012,603 B2 * | 3/2006 | Chen et al. ............ 345/419 |
| 7,079,704 B2 * | 7/2006 | Caviedes ............... 382/280 |
| 7,620,443 B2 * | 11/2009 | Kokubun et al. ........ 600/428 |
| 2003/0122824 A1 * | 7/2003 | Chen et al. ............ 345/428 |
| 2008/0056547 A1 * | 3/2008 | Kokubun et al. ........ 382/128 |

FOREIGN PATENT DOCUMENTS

| | | |
|---|---|---|
| DE | 198 54 939 A1 | 6/2000 |
| DE | 102 07 623 A1 | 11/2003 |
| EP | 1 394 747 A1 | 3/2004 |

* cited by examiner

*Primary Examiner*—Samir A Ahmed
*Assistant Examiner*—Li Liu
(74) *Attorney, Agent, or Firm*—Harness, Dickey & Pierce, P.L.C.

(57) ABSTRACT

A method is for generating tomograms of a cyclically and complexly moving examination object using a tomography unit that reconstructs tomograms in at least one slice plane from detector output data. At least two tomograms from different phases of the movement cycle of the examination object are reconstructed in the region of at least one slice plane. The tomograms are subdivided automatically into subregions with good and bad image quality, and at least one complete tomogram is assembled from subregions with relatively good image quality per slice plane.

23 Claims, 3 Drawing Sheets

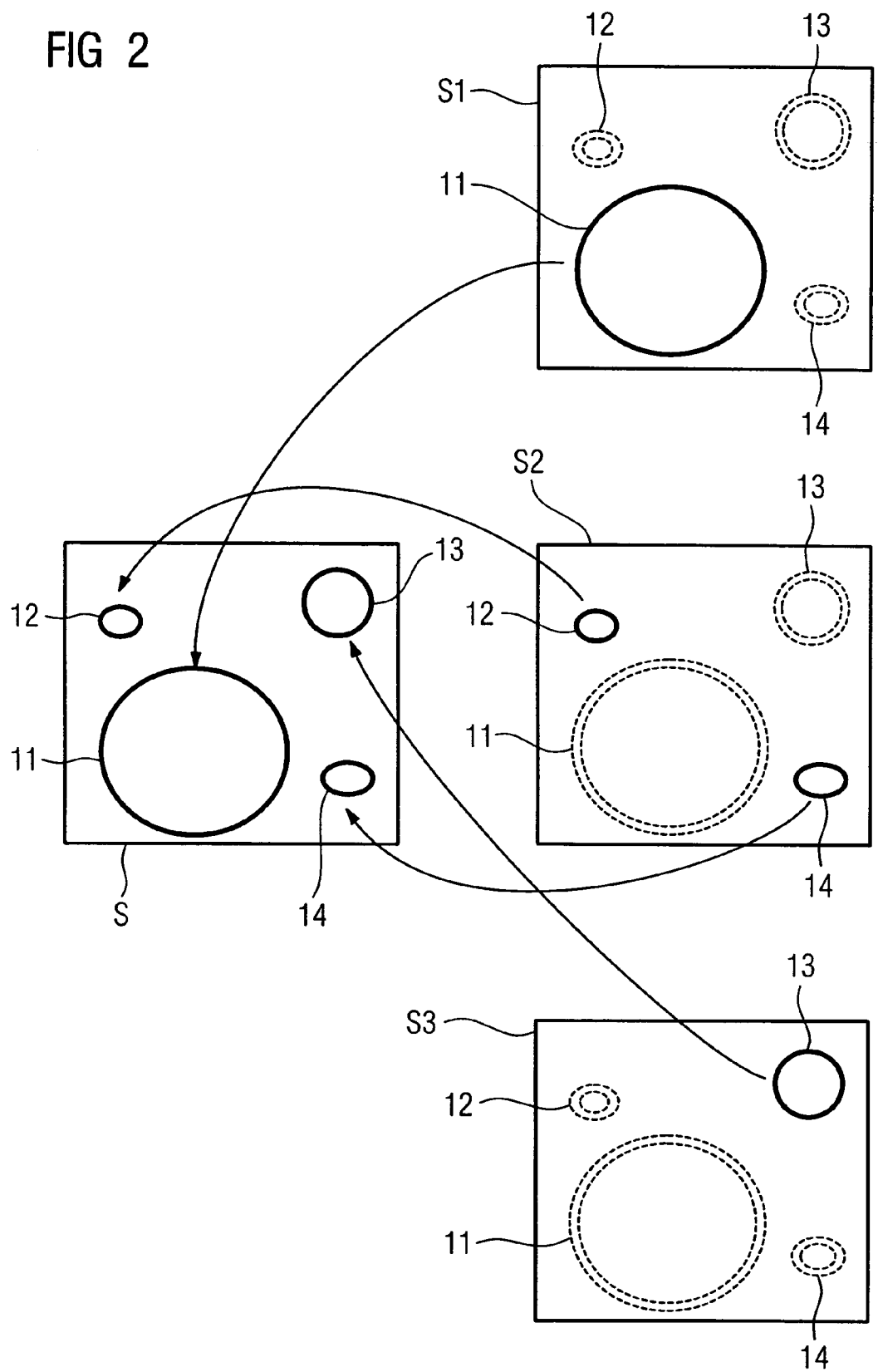

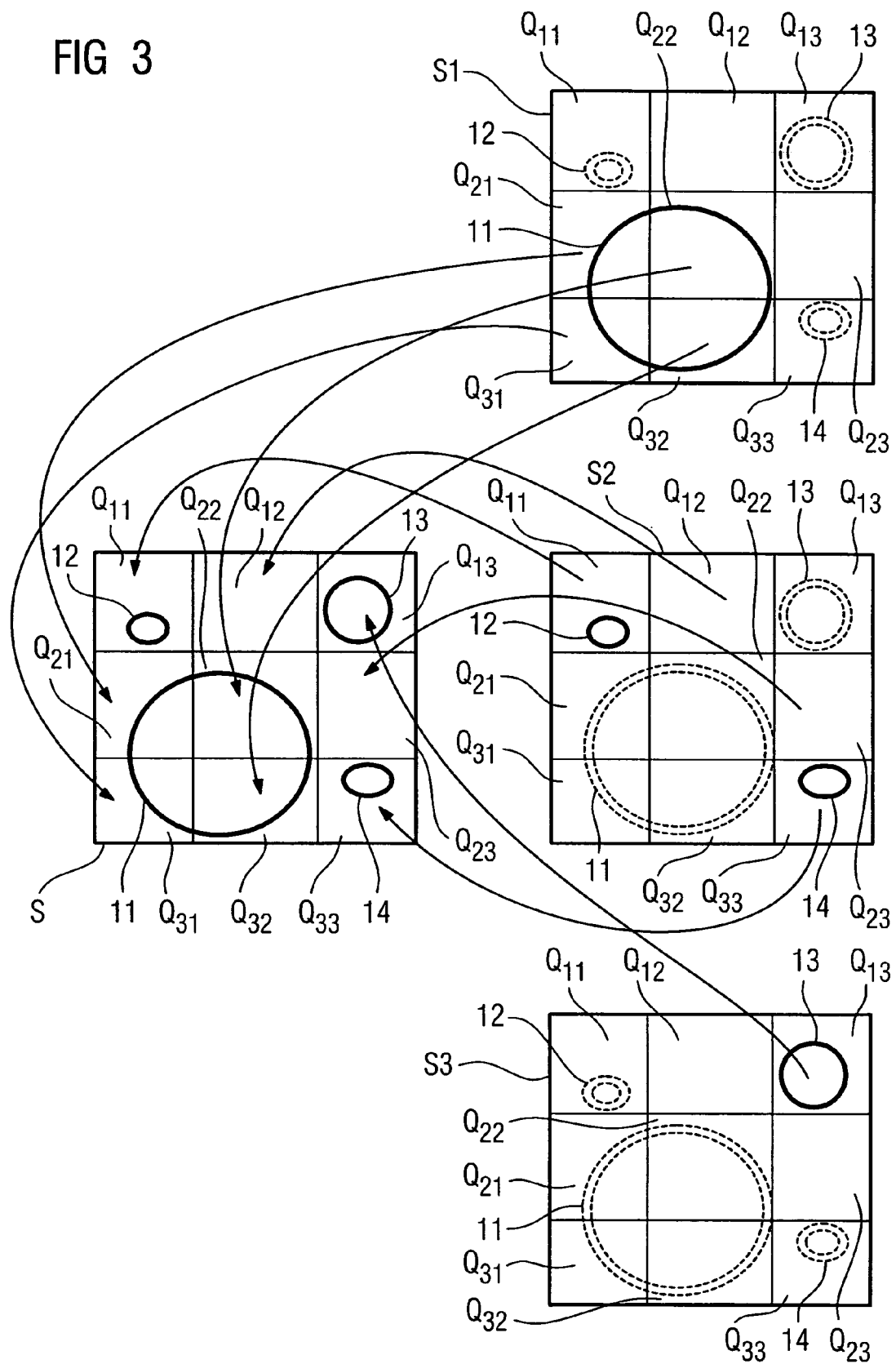

METHOD FOR OPTIMIZING THE DISPLAY OF FLAT SLICES OF A CYCLICALLY AND COMPLEXLY MOVING EXAMINATION OBJECT FROM DETECTOR MEASURED DATA OF A TOMOGRAPHY UNIT

The present application hereby claims priority under 35 U.S.C. §119 on German patent application number DE 10 2004 028 121.1 filed Jun. 9, 2004, the entire contents of which is hereby incorporated herein by reference.

FIELD

The invention generally relates to a method for optimizing the display of flat slices of a cyclically and complexly moving examination object from detector measured data of a tomography unit. In one example, at least one radiation source emits a beam having rays that vary during passage through the examination object, at least one opposite at least one-row detector measures the intensity variation of the rays after the penetration of the examination object, at least the radiation source, preferably also the detector, revolves around the examination object on an imaginary cylindrical surface, preferably also at least one circular track or one spiral track, and scans this examination object in so doing, and detector output data are reconstructed to form at least one tomogram in the region of at least one slice plane.

BACKGROUND

Methods are generally known. Reference may be made by way of example to the laid-open patent applications DE 198 54 939 A1 and DE 102 07 623 A1. In these known methods, an attempt is made during scanning of the moving examination object to freeze the movement of a complexly moving object, this usually being a beating human heart. This freezing is based on the fact that the object moves little during a sufficiently long time period, that is to say a certain cardiac phase. Data that were recorded during this time period are then used during the reconstruction.

However, practice has shown that the time period in which a single image is generated is nevertheless too long, and so at least individual regions of the images are unsharply imaged nevertheless because of an unavoidable movement of the object.

SUMMARY

An object of an embodiment of the invention is to present a method for reconstructing tomograms of a cyclically and complexly moving examination object from detector measured data of a tomography unit that generates tomograms with increased sharpness.

The inventors have realized that a substantial problem in the imaging of such complexly moving objects such as a beating heart, for example, resides in that the movement of the object takes place in different phases of the movement cycle depending on the subregion of the object being viewed. Correspondingly, it is also the case that different parts of the object such as, for example, atrium or coronary arteries, are at rest in different phases of the movement cycle.

In order to obtain an improved or even optimum CT image, one embodiment of the application proposes to reconstruct a number of tomograms in the region of a slice plane over the entire movement cycle of the complexly moving object, and to search these tomograms respectively for the object regions most favorable in terms of the display; and to generate therefrom overall a single tomogram that includes a mixture of improved or even optimally displayed regions of different movement cycles. The quality of the imaging in different regions is undertaken in this case automatically by image analysis.

In accordance with this basic idea, an embodiment of the application proposes to improve methods known per se for improving or even optimizing the display of flat slices of a cyclically and complexly moving examination object from detector measured data of a tomography unit, in which case at least one radiation source emits a beam having rays that vary during passage through the examination object. At least one opposite at least one-row detector measures the intensity variation of the rays after the penetration of the examination object. Further, at least the radiation source, which for example may also be the detector, revolves around the examination object on an imaginary cylindrical surface, for example at least one circular track or one spiral track. It then scans this examination object in so doing.

A computer unit then reconstructs detector output data to form at least one tomogram in the region of at least one slice plane. At least two tomograms from different phases of the movement cycle of the examination object are reconstructed in the region of at least one slice plane. The tomograms compiled in this at least one slice plane are subdivided automatically into subregions, and a complete tomogram is assembled per slice plane from subregions of the individual tomograms. For this purpose, use is made of the subregions of the individual tomograms that respectively exhibit relatively the best image quality of the respective subregion.

It may be pointed out that the term "complex movement" in the sense of the application is to be understood, for example, as a movement of an examination object in the case of which different subregions of the examination object move or are at rest at different times of the movement cycle.

The effect of this method according to an embodiment of the invention is that it is possible to assemble from a number of tomograms that are compiled in the region of a slice plane and which, regarded per se, exhibit different regions of different image quality, an aggregate image that respectively exhibits overall the best possible image quality of the tomograms reconstructed in total from different cycle areas.

The term "image quality" can be understood, for example, as a measure of the unsharpness, preferably the movement unsharpness, in the subregion respectively being viewed. However, it is also possible for "image quality" to be understood as the presence of the strength of occurring image artifacts. This image quality can be taken directly from the image data, for example.

Thus, for example, it is possible to carry out over subregions of the image a Fourier analysis from which, for example, a measure of the unsharpness can be taken. However, it is also possible, on the other hand, in addition or alternatively to determine the image quality from the knowledge of the complex movement behavior in relation to the movement cycle of the examination object, and/or from the recording instant of the recorded tomograms in relation to the movement cycle.

Thus, from the knowledge that specific organic structures are moving in specific cycle phases, the regions of these organic structures that are known to be moving in a specific movement cycle are defined as negative without special measurement of the actual image quality. Further, these regions may be excluded from the start for the assembly of the improved or even optimum result image. Conversely, it is also possible for organic structures or subregions of the image that are known to be in an optimum rest situation in a specific cycle phase, preferably to be used to assemble the result image.

In order to observe the movement cycle, it is possible, for example, to use a parallel recording of an ECG, or to take the movement cycle from the detector data themselves, preferably from the measurement of temporally offset, preferably also counter-running beams of the same path. Such measurement methods are adequately described in the prior art.

In accordance with a further variant of the method according to an embodiment of the invention, the inventors propose that the reconstructed tomograms from one slice plane and different cycle phases are subdivided into a multiplicity of image segments. For each image segment, the mean or maximum image quality of each segment in each tomogram may be measured automatically. Further, an aggregate tomogram of this slice plane may be assembled from the segments with best image quality.

Such a method is suitable with particular ease for the automated improvement or mixing of result images. This is because it is possible without special pattern recognition methods to raster the CT image into a multiplicity of image segments and to measure the image quality, in particular the existing image sharpness or unsharpness, with particular ease by way of the image segments. Further, subsequently segments may be selected which are respectively most improved or even optimum for assembling the aggregate image.

In another variant of an embodiment of the method, the inventors propose that a pattern recognition method is used in at least two tomograms from different cycle phases of the same slice plane to determine at least one region that is typically moved during the corresponding cycle phase. In the process, at least one region may be replaced by the same section of another tomogram of the same slice plane.

As an alternative to this, it is also possible that an image analysis method is used in at least two tomograms from different cycle phases of the same slice plane to determine at least one identical region in which the image quality of the tomograms is different. Further, the image of the best tomogram may be taken as the result image for this region.

The inventors also propose, in another embodiment, during assembly of the complete tomogram from subregions or partial images, to match the transitions between the subregions or image segments to one another. In this context, a simple interpolation at the boundaries between the subregions may take place in the region of the transitions between the subregions, for example.

It may be pointed out in addition that in the sense of at least one embodiment of the invention, the tomograms from different cycle phases need not necessarily originate from a single movement cycle. They can also originate from a number of movement cycles that preferably occur one after another. Likewise, the slice planes of the tomograms need not necessarily be exactly identical. It suffices when the slice planes originate from a single volume that is sufficiently narrow in the z-direction, if appropriate the slice planes can also be matched by way of a preceding interpolation method.

In accordance with the basic idea of at least one embodiment of the invention, a tomography unit, preferably a CT unit, is proposed for reconstructing tomograms from detector measured data for the purpose of improvement. In this case, the known tomography unit includes at least one radiation source that generates a beam and can be rotated about a system axis. Furthermore, it has at least one opposite at least one-row detector that measures the absorption of the rays emanating from the radiation source after penetration of an examination object, and at least one device, for example at least one computer unit, for controlling the tomography unit, as well as collecting and computationally processing the detector output data, reconstructing tomograms of at least one slice plane and for displaying the images. According to at least one embodiment of the invention, an improvement of this tomography unit may reside in program segments for carrying out the method outlined above.

BRIEF DESCRIPTION OF THE DRAWINGS

The invention is described in more detail below with the aid of the exemplary embodiments and of the figures, it being pointed out that only the elements essential for the direct understanding of the invention are shown. The following reference symbols are used in this case: 1: computer-tomography unit; 2: X-ray tube; 3: detector; 4: system axis or z-axis; 5: housing; 6: patient couch; 7: patient; 8: ECG measuring lead; 9: computer unit; 9.1: display screen; 9.2: input unit; 10: data and control line; 11-16: organic structures of the examination object; $P_1$-$P_n$: program modules; S: result image/assembled aggregate image; $S_1$-$S_3$: tomograms from different cycle phases; $Q_{11}$-$Q_{33}$: subsegments of the tomograms.

In detail:

FIG. 2 shows a schematic illustration of the method according to an embodiment of the invention with pattern recognition of individual organic structures; and FIG. 3 shows an illustration of the method according to an embodiment of the invention with division of the tomograms that resembles a chess board.

DETAILED DESCRIPTION OF THE EXAMPLE EMBODIMENTS

Figure 1:
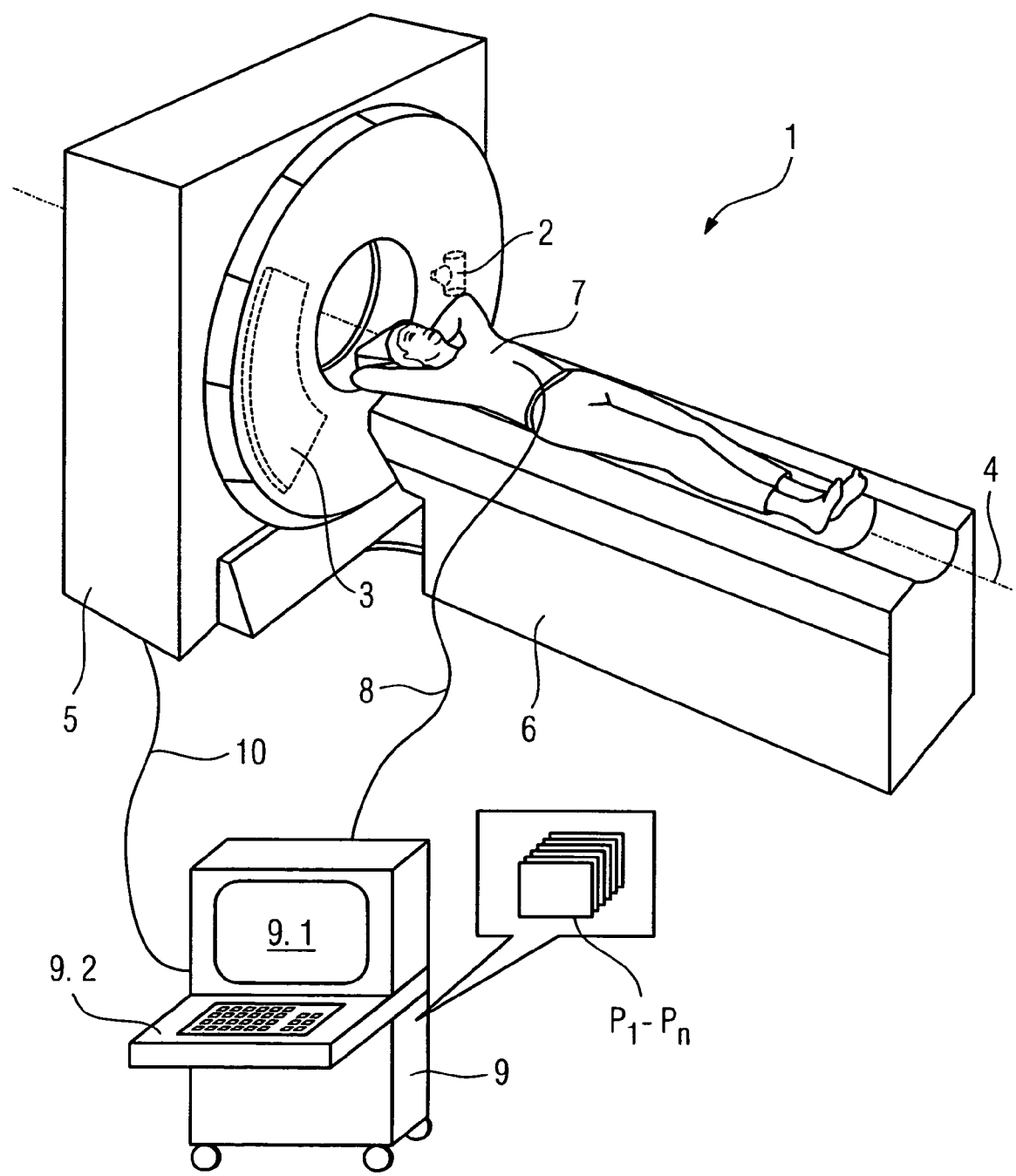
FIG. 1 shows an illustration of a CT for carrying out the method according to an embodiment of the invention.

FIG. 1 shows a 3D illustration of a computer-tomography unit 1 having an X-ray tube 2 that serves here, for example, as a radiation source, and an opposite detector 3, two of which are fastened on a rotary frame (not visible) and designed to be capable of rotation about a system axis or z-axis 4. The patient 7 is located on a patient couch 6, which can be displaced along the z-axis 4, and is pushed through an opening in the housing 5 of the computerized tomography while the X-ray tube 2 and the detector 3 rotate about the system axis 4, this being done such that the X-ray tube 2 and the detector 3 move relative to the patient on a spiral track about this patient and scanning is performed in the process.

It is to be remarked in principle that other variants of the scanning are possible in conjunction with the method presented at the beginning. Thus, for example, sequential scanning can be performed by moving the X-ray tube 2 and the detector 3 in a circular fashion around the patient 7 and advancing the patient in a discrete step along the system axis 4 after a complete circular scan. Thereafter, a circular scan may be carried out once again until the patient or at least the examination region being viewed, is completely scanned. If use is made of a detector having a large number of detector rows, that is to say having a large extent in the direction of the z-axis, it is also possible, if appropriate, for at least the heart region being viewed here in particular to be completely scanned with the aid of a single rotation of the detector.

In addition to the scanning of the patient with the aid of X-rays, the cardiac activity of the patient is recorded by way of electrodes (not illustrated in detail) and a measuring lead 8 in an ECG. In the present example, this ECG is located in a computer unit 9 that simultaneously also controls the computerized tomography.

In addition to controlling the computerized tomography and to recording an ECG, the computer unit 9 also serves for evaluating and, if appropriate, storing the detector output data, this being done via a data and control line 10. The computer unit 9 can also be used to carry out the reconstruction of the tomograms. This purpose is served by the schematically illustrated programs $P_1$ to $P_n$, it being possible for the results to be displayed on the display screen 9.1 integrated in the computer unit 9. The input unit 9.2, for example in the form of a keyboard and/or a computer mouse not illustrated explicitly here, can be used to input data in order to operate the computerized tomography.

All the described variants with spiral or sequential circular scanning and single-row up to multirow detectors can be used in conjunction with the method according to an embodiment of the invention, although it is necessary in each case to view the same slice several times in each case during a movement cycle in order to obtain at least two tomograms from different cycle phases. Instead of the ECG, the movement information can also be taken directly from the detector data in order to determine the cycle phase.

FIG. 2 shows a schematic illustration of the method according to an embodiment of the invention, in which three different tomograms $S_1$, $S_2$ and $S_3$ have respectively been reconstructed from different cycle phases during a complete cycle. These tomograms are subsequently subdivided with the aid of a pattern recognition method into regions in which individual organic structures such as, for example, the cardiac atrium and the coronary arteries, are located. It is shown in the illustration that, for example, the organic structure 11 is sharply displayed in the first tomogram $S_1$, while the organic structures 12, 13 and 14 are unsharply imaged because of movement unsharpness or other image artifacts. In the tomogram $S_2$ of a further phase of the movement cycle, the organic structures 11 and 13 are imaged unsharply, while the organic structures 12 and 14 are imaged sharply and, finally, only the organic structure 3 is sharply displayed in the tomogram $S_3$, while the other organic structures are displayed with little image quality.

According to an embodiment of the invention, there are now respectively selected from the existing tomograms $S_1$ to $S_3$ the regions that are best designed with reference to their image quality and—as illustrated by the arrows—are assembled to form an aggregate image S. This produces an aggregate image that has in each case extracted the most favorable regions from the three phase images $S_1$ to $S_3$ with reference to image quality, and leads overall to an image S with optimum image quality.

FIG. 3 shows a method according to an embodiment of the invention that is similar to FIG. 2, but there is no need here for a pattern recognition method that recognizes individual organic structures and assigns corresponding regions. In this method, the individual tomograms $S_1$ to $S_3$ of the different phases of a movement cycle are arbitrarily divided into a chequerboard pattern. A division having 3×3 segments is shown here by ways of example. However, it is to be anticipated that it is more favorable to undertake a finer division than the one now shown here.

In accordance with this method illustrated here, for each individual subsegment $Q_{11}$ to $Q_{33}$ the image quality is compiled by an image analysis over the respective segment and the subsegment that turns out to be most favorable with reference to its image quality is subsequently respectively selected from the existing set of tomograms that are arranged in the same slice plane. Thus, for example, there is selected from the number of segments $Q_{11}$ of the tomograms $S_1$, $S_2$ and $S_3$ the one which exhibits the highest image quality. This corresponds in the present example to the subsegment $Q_{11}$ from the tomogram $S_2$.

This method is carried out for all the subsegments $Q_{11}$ to $Q_{33}$ and an aggregate image S that respectively comprises the partial images with the highest image quality is then assembled. According to an embodiment of the invention, it is possible in addition to carry out a matching in the edge regions such that no transitions can be recognized between the individual edge regions.

Thus, overall, an embodiment of this invention presents a method for generating tomograms from a cyclically and complexly moving examination object by way of a tomography unit that reconstructs tomograms in at least one slice plane from detector output data, at least two tomograms of different phases of the movement cycle of the examination object being reconstructed in the region of at least one slice plane, the tomograms being subdivided automatically into subregions with good and poor image quality, and at least one complete tomogram being assembled per slice plane from subregions with good image quality. Thus, it is thereby now possible to compile from a number of tomograms of different phases in the same slice plane that respectively have different regions with greater or poorer image quality an aggregate image that is assembled from regions with the respectively most favorable image qualities of the sum of all the tomograms in the region of a slice plane, and therefore itself exhibits an aggregate image quality that is better than all the individual images.

It goes without saying that the abovementioned features of an embodiment of the invention can be used not only in the combination respectively specified, but also in other combinations or on their own, without departing from the scope of the invention.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for improving display of flat slices of a cyclically and complexly moving examination object from detector measured data of a tomography unit, the method comprising:
reconstructing, by a processing unit, at least two tomograms from different phases of a movement cycle of the examination object in a region of at least one slice plane,
automatically subdividing, by said processing unit, the tomograms of the at least one slice plane into an arbitrary N by N pattern of subregions, N being an integer value; and
assembling, by said processing unit, a complete tomogram per slice plane from the arbitrary pattern of subregions of the individual tomograms, the arbitrary pattern of subregions of the individual tomograms exhibiting the relatively best image quality being used, the image quality being determined from the knowledge of the complex movement behavior in relation to the movement cycle of the examination object, and from the recording instant of the recorded tomograms in relation to the movement cycle.

2. The method as claimed in claim 1, wherein the image quality is determined by a measure of unsharpness, preferably the movement unsharpness.

3. The method as claimed in claim 2, wherein the image quality is also determined by the strength of occurring image artifacts.

4. The method as claimed in claim 2, wherein the image quality is also taken directly from the image data.

5. The method as claimed in claim 1, wherein the image quality is determined by the strength of occurring image artifacts.

6. The method as claimed in claim 5, wherein the image quality is taken directly from the image data.

7. The method as claimed in claim 1, wherein the image quality is taken directly from the image data.

8. The method as claimed in claim 1, wherein the movement cycle is measured by parallel recording of an ECG.

9. The method as claimed in claim 8, wherein the movement cycle is taken from the measurement of temporally offset counter-running rays of the same path.

10. The method as claimed in claim in claim 1, wherein the movement cycle is taken from detector data of a detector of the tomography unit.

11. The method as claimed in claim 1, wherein the reconstructed tomograms from one slice plane and different cycle phases are subdivided into a multiplicity of image segments, and for each segment of all the tomograms, the mean or maximum image quality of each segment in each tomogram is measured automatically, and an aggregate tomogram of this slice plane is assembled from the segments with the relatively best image quality.

12. The method as claimed in claim 1, wherein a pattern recognition method is used in at least two tomograms from different cycle phases of the same slice plane to determine at least one region that is typically moved during the corresponding cycle phase, and this at least one region is replaced by the same section of another tomogram of the same slice plane.

13. The method as claimed in claim 1, wherein an image analysis method is used in at least two tomograms from different cycle phases of the same slice plane to determine at least one identical region in which the image quality of the tomograms is different, and the image of the relatively best tomogram is adopted as the result image for this region.

14. The method as claimed in one claim 1, wherein, during assembly of the complete tomogram from at least two of the arbritrary pattern of subregions, the transitions between the at least two of the arbitrary pattern of subregions are matched to one another.

15. The method as claimed in claim 1, wherein the image quality is determined by a measure of movement unsharpness.

16. The method as claimed in claim 15, wherein the image quality is also determined by the strength of occurring image artifacts.

17. The method as claimed in claim 1, wherein
at least one radiation source emits a beam having rays that vary during passage through the examination object,
at least one opposite at least one-row detector measures the intensity variation of the rays after the penetration of the examination object,
at least the radiation source revolves around and scans the examination object on an imaginary cylindrical surface, and
said processing unit reconstructs detector output data to form at least one tomogram in the region of at least one slice plane.

18. A computer readable medium including a computer executable program, adapted to carry out the method as claimed in claim 1.

19. A tomography unit, comprising:
at least one radiation source that generates a beam, for rotation about a system axis;
at least one-row detector to measure the absorption of the rays emanating from the radiation source after penetration of an examination object;
at least one means for controlling the tomography unit, and for collecting and computationally processing detector output data, reconstructing tomograms of at least one slice plane and displaying the images, the at least one means being programmed to carry out the method as claimed in claim 1.

20. The tomography unit of claim 19, wherein the tomography unit is an X-ray computer-tomography unit.

21. A tomography unit, comprising:
means for reconstructing at least two tomograms from different phases of a movement cycle of the examination object in the region of at least one slice plane;
means for automatically subdividing the tomograms of the at least one slice plane into an arbitrary N by N pattern of subregions, N being an integer value; and
means for assembling a complete tomogram per slice plane from the arbitrary pattern of subregions of the individual tomograms, the subregions of the individual tomograms exhibiting the relatively best image quality being used, the image quality being determined from the knowledge of the complex movement behavior in relation to the movement cycle of the examination object, and from the recording instant of the recorded tomograms in relation to the movement cycle.

22. The tomography unit of claim 21, further comprising:
at least one radiation source, to emit a beam having rays that vary during passage through the examination object; and
at least one opposite at least one-row detector to measure the intensity variation of the rays after the penetration of the examination object, the at least the radiation source being further for revolving around and scanning the examination object on an imaginary cylindrical surface.

23. The tomography unit of claim 21, further comprising:
means for emitting a beam having rays that vary during passage through the examination object; and
means for measuring the intensity variation of the rays after the penetration of the examination object, the means for emitting further being for revolving around and scanning the examination object on an imaginary cylindrical surface.

* * * * *